United States Patent
Chapple et al.

(10) Patent No.: US 7,153,819 B2
(45) Date of Patent: Dec. 26, 2006

(54) STABILIZATION OF ANTIBODIES OR FRAGMENTS THEREOF

(75) Inventors: Andrew Paul Chapple, Bebington (GB); Sandra Hemmington, Shambrook (GB); Steven Howell, Northants (GB); Neil James Parry, Shambrook (GB)

(73) Assignee: Unilever Home & Personal Care USA divison of Conopco, Inc., Greenwich, CT (US)

(*) Notice: Subject to any disclaimer, the term of this patent is extended or adjusted under 35 U.S.C. 154(b) by 284 days.

(21) Appl. No.: 10/025,237

(22) Filed: Dec. 19, 2001

(65) Prior Publication Data

US 2002/0155968 A1 Oct. 24, 2002

(30) Foreign Application Priority Data

Dec. 19, 2000 (EP) .................................. 00311407

(51) Int. Cl.
*C11D 3/00* (2006.01)
*C11D 17/00* (2006.01)
*G01N 33/53* (2006.01)

(52) U.S. Cl. ...................... 510/392; 510/305; 510/337; 510/418; 435/7.22

(58) Field of Classification Search ................ 510/392, 510/305, 418, 337; 435/7.22
See application file for complete search history.

(56) References Cited

U.S. PATENT DOCUMENTS 3,715,279 A 2/1973 Suzuki et al. .................. 195/68
4,397,959 A * 8/1983 Hechemy .................... 435/7.22
5,445,747 A * 8/1995 Kvietok et al. ............. 510/101
5,476,608 A * 12/1995 Boyer et al. ................. 510/321
6,218,350 B1 * 4/2001 Beggs et al. ................ 510/305

FOREIGN PATENT DOCUMENTS

| EP | 194 276 | 1/2002 |
|---|---|---|
| WO | 94/04678 | 3/1994 |
| WO | 94/25591 | 11/1994 |
| WO | 94/29457 | 12/1994 |
| WO | 98/06811 | 2/1998 |
| WO | 98/56885 | 12/1998 |
| WO | 00/02984 | 1/2000 |

OTHER PUBLICATIONS

Protein Engineering, *Single antibody domains as small recognition units: design and in vitro antigen selection of camelized, human VH domains with improved protein stability*, Julian Davies and Lutz Riechmann, vol. 9, pp. 531-537, 1996.
Bio/Technology, *Antibody VH Domains as Small Recognition Units*, Julian Davies and Lutz Riechmann, May 13, 1995, pp. 475-479.
Proc. National Academy of Science, *"Diabodies": Small bivalent and bispecific antibody fragments*, Philipp Holiger et al., vol. 90, Jul. 1993, pp. 6444-6448.
PCT International Search Report in a PCT application PCT/EP 01/14478.

* cited by examiner

*Primary Examiner*—Douglas McGinty
*Assistant Examiner*—Preeti Kumar
(74) *Attorney, Agent, or Firm*—Rimma Mitelman (57) ABSTRACT

There is provided an antibody granule, consisting essentially of one or more antibodies, or fragments derived thereof, granulated with an alkali metal salt. Also provided is a process for preparing said antibody granules. The granules can be used in an enzymatic stain bleaching or anti dye-transfer composition.

10 Claims, 4 Drawing Sheets

STABILIZATION OF ANTIBODIES OR FRAGMENTS THEREOF

TECHNICAL FIELD

The present invention generally relates to the stabilisation of antibodies, or fragments derived thereof, in detergent compositions, in particular in bleaching detergent compositions.

BACKGROUND AND PRIOR ART

Antibodies are polypeptides which are capable of binding specifically to compounds against which they were raised. Antibodies are used for a variety of purposes, such as immuno assays. More recently, their application in detergent and cleaning applications has been proposed. WO-A-98/56885 (Unilever) discloses a bleaching enzyme which is capable of generating a bleaching chemical and having a high binding affinity for stains present on fabrics, as well as an enzymatic bleaching composition comprising said bleaching enzyme, and a process for bleaching stains on fabrics. The binding affinity may be formed by a part of the polypeptide chain of the bleaching enzyme, or the enzyme may comprise an enzyme part which is capable of generating a bleach chemical that is coupled to a reagent having the high binding affinity for stains present on fabrics. In the latter case, the reagent may be bi-specific, comprising one specificity for stain and one for enzyme. Examples of such bi-specific reagents mentioned in the disclosure are antibodies, especially those derived from Camelidae having only a variable region of the heavy chain polypeptide ($V_{HH}$), peptides, peptidomimics, and other organic molecules. The enzyme usually is an oxidase, such as glucose oxidase, galactose oxidase and alcohol oxidase, which is capable of forming hydrogen peroxide or another bleaching agent. Thus, if the multi-specific reagent is an antibody, the enzyme forms an enzyme/antibody conjugate which constitutes one ingredient of a detergent composition. During washing, said enzyme/antibody conjugate of the detergent composition is targeted to stains on the clothes by another functional site of the antibody, while the conjugated enzyme catalyses the formation of a bleaching agent in the proximity of the stain and the stain will be subjected to bleaching.

Little attention has been paid so far to the manner in which such antibodies are added to the detergent composition in order to achieve the desired bleaching effect of the enzyme-antibody complex. It was found that the storage stability of the antibodies in such cleaning compositions problem is not always satisfactory. Extensive prior art exists regarding the granulation of enzymes for use in detergents, but this technology cannot be directly transferred to antibodies.

The purpose of the present invention is to provide a method by which antibodies can be incorporated into (bleaching) detergent compositions in a stable manner.

It has now surprisingly been found that it is possible to incorporate antibodies into detergent compositions in a stable manner if the antibodies are granulated with simple salts, such as sodium or potassium salts. This is the converse to granulation of enzymes, whereby complicated measures have to be taken in the granulation technology in order to provide the required stability and the lifetime of the enzyme.

Moreover, it was surprisingly found the antibody activity was improved when they were stored in the granulated form, as compared to common protein storage methods. This therefore imparts a substantially improved lifetime of the antibody and its associated performance in a powdered form or product form.

DEFINITION OF THE INVENTION

According to a first aspect of the invention, there is provided an antibody granule consisting essentially of one or more antibodies, or fragments derived thereof, granulated with an alkali metal salt.

According to a second aspect, there is provided an enzymatic stain bleaching or anti dye-transfer composition comprising the antibody granule.

According to a third aspect, there is provided a process for preparing said antibody granules.

DESCRIPTION OF THE INVENTION

In its first aspect, the invention relates to an antibody granule consisting essentially of one or more antibodies, or fragments derived thereof, granulated with an alkali metal salt. As stated above, antibodies are polypeptides which are capable of binding specifically to compounds against which they were raised. For the purpose of this invention, "antibodies" also includes fragments of antibodies and fusion proteins of antibodies with enzymes, such as disclosed in WO-A-98/56885. "antibodies" also includes other polypeptides which have a high binding affinity for specific other molecules or structures, for instance cellulose binding domains (CBD's) which occur in cellulases.

The degree of binding of a compound A to another molecule B can be generally expressed by the chemical equilibrium constant $K_d$ resulting form the following binding reaction:

$$[A]+[B] \leftrightharpoons [A::B]$$

The chemical equilibrium constant $K_d$ is then given by:

$$K_d = \frac{[A] \times [B]}{[A::B]}$$

Whether the binding to the substance is specific or not can be judged from the difference between the binding ($K_d$ value) of the compound to that substance, versus the binding to the material to which that substance is applied, or versus other substances one does not want to oxidise. For substances which occur in stains, the latter material can be envisioned to be the fabric on which the stain is present, or the dye molecules on coloured garments. The difference between the two binding constants should be minimally 100, and preferably more that 1000. Typically, the compound should bind the coloured substance with a $K_d$ value of $1*10^{-4}$ to $1*10^{-6}$, with a background binding to fabric with a $K_d$ of $1*10^{-2}$ to $1*10^{-3}$. Higher binding affinities ($K_d$ of less than $1*10^{-5}$) and/or a larger difference between coloured substance and background binding would increase the selectivity of the oxidation process. Also, the weight efficiency of the compound in the total detergent composition would be increased and smaller amounts of the compound would be required.

Antibodies can be derived from several sources. From mice, monoclonal antibodies can be obtained which possess very high binding affinities. From such antibodies, Fab, Fv or scFv fragments, can be prepared which have retained their binding properties. Such antibodies or fragments can be produced through recombinant DNA technology by microbial fermentation. Well known production hosts for antibodies and their fragments are yeast, moulds or bacteria.

A class of antibodies of particular interest is formed by the Heavy Chain antibodies as found in Camelidae, like the camel or the llama. The binding domains of these antibodies consist of a single polypeptide fragment, namely the variable region of the heavy chain polypeptide (HC-V). In contrast, in the classic antibodies (murine, human, etc.), the binding domain consist of two polypeptide chains (the variable regions of the heavy chain ($V_h$) and the light chain ($V_l$)). Procedures to obtain heavy chain immunoglobulins from Camelidae, or (functionalized) fragments thereof, have been described in WO-A-94/04678 (Casterman and Hamers) and WO-A-94/25591 (Unilever and Free University of Brussels).

Alternatively, binding domains can be obtained from the $V_h$ fragments of classical antibodies by a procedure termed "camelization". Hereby the classical $V_h$ fragment is transformed, by substitution of a number of amino acids, into a HC-V-like fragment, whereby its binding properties are retained. This procedure has been described by Riechmann et al. in a number of publications (J. Mol. Biol. (1996) 259, 957–969; Protein. Eng. (1996) 9, 531–537, Bio/Technology (1995) 13, 475–479). Also HC-V fragments can be produced through recombinant DNA technology in a number of microbial hosts (bacterial, yeast, mould), as described in WO-A-94/29457 (Unilever).

Methods for producing fusion proteins that comprise an enzyme and an antibody or that comprise an enzyme and an antibody fragment are already known in the art. One approach is described by Neuberger and Rabbits (EP-A-194 276). A method for producing a fusion protein comprising an enzyme and an antibody fragment that was derived from an antibody originating in Camelidae is described in WO-A-94/25591. A method for producing bi-specific antibody fragments is described by Holliger et al. (1993) PNAS 90, 6444–6448.

A particularly attractive feature of antibody binding behaviour is their reported ability to bind to a "family" of structurally-related molecules. For example, in Gani et al. (J. Steroid Biochem. Molec. Biol. 48, 277–282) an antibody is described that was raised against progesterone but also binds to the structurally-related steroids, pregnanedione, pregnanolone and 6-hydroxy-progesterone. Therefore, using the same approach, antibodies could be isolated that bind to a whole "family" of stain chromophores (such as the polyphenols, porphyrins, or caretenoids as described below). A broad action antibody such as this could be used to treat several different stains when coupled to a bleaching enzyme.

Several classes of other compounds can be envisaged which deliver the specific binding capability. In the following we will give a number of examples of such other compounds having such binding capabilities, without pretending to be exhaustive.

1. Peptides

Peptides usually have lower binding affinities to the substances of interest than antibodies. Nevertheless, the binding properties of peptides can be sufficient to deliver the desired binding effect. A peptide which is capable of binding selectively to another substance can for instance be obtained from a protein which is known to bind to that specific substance. An example of such a peptide would be a binding region extracted from an antibody raised against that substance.

Alternatively, peptides which bind to such substance can be obtained by the use of peptide combinatorial libraries. Such a library may contain up to $10^{10}$ peptides, from which the peptide with the desired binding properties can be isolated. (R. A. Houghten, Trends in Genetics, Vol 9, no.7, 235–239). Several embodiments have been described for this procedure (J. Scott et al., Science (1990), Vol. 249, 386–390; Fodor et al., Science (1991), Vol. 251, 767–773; K. Lam et al., Nature (1991) Vol. 354, 82–84; R. A. Houghten et al., Nature (1991) Vol. 354, 84–86).

Suitable peptides can be produced by organic synthesis, using for example the Merrifield procedure (Merrifield, J.Am.Chem.Soc. (1963), 85, 2149–2154). Alternatively, the peptides can be produced by recombinant DNA technology in microbial hosts (yeast, moulds, bacteria)(K. N. Faber et al., Appl. Microbiol. Biotechnol. (1996) 45, 72–79).

2. Pepidomimics

In order to improve the stability and/or binding properties of a peptide, the molecule can be modified by the incorporation of non-natural amino acids and/or non-natural chemical linkages between the amino acids. Such molecules are called peptidomimics (H. U. Saragovi et al. Bio/Technology (1992), Vol 10, 773–778; S. Chen et al., Proc.Natl.Acad. Sci. USA (1992) Vol 89, 5872–5876). The production of such compounds is restricted to chemical synthesis.

3. Other Organic Molecules

It can be readily envisaged that other molecular structures, which need not be related to proteins, peptides or derivatives thereof, can be found which bind selectively to substances. For example, certain polymeric RNA molecules which have been shown to bind small synthetic dye molecules (A. Ellington et al., Nature (1990) vol. 346, 818–822). Such binding compounds can be obtained by the combinatorial approach, as described for peptides (L. B. McGown et al., Analytical Chemistry, Nov. 1, 1995, 663A–668A).

This approach can also be applied for purely organic compounds which are not polymeric. Combinatorial procedures for synthesis and selection for the desired binding properties have been described for such compounds (Weber et al., Angew.Chem.Int.Ed.Engl. (1995), 34, 2280–2282; G. Lowe, Chemical Society Reviews (1995) Vol 24, 309–317; L.A. Thompson et al. Chem. Rev. (1996), Vol. 96, 550–600). Once suitable binding compounds have been identified, they can be produced on a larger scale by means of organic synthesis.

When using the approach disclosed in WO-A-98/56885 (Unilever), the antibodies are directed at stains present on fabrics. Several classes of substances one would like to oxidise can be envisaged: For detergents applications, coloured or non-coloured substances which may occur as stains on fabrics can be a target. Several types or classes of coloured substances which may occur in stains can be envisaged:

1. Porphyrin Derived Structures.

Porphyrin structures, often coordinated to a metal, form one class of coloured substances which occur in stains. Examples are heme or haematin in blood stain, chlorophyll as the green substance in plants, e.g. grass or spinach. Another example of a metal-free substance is bilirubin, a yellow breakdown product of heme.

2. Tannins, Polyphenols

Tannins are polymerised forms of certain classes of polyphenols. Such polyphenols are catechins, leuantocyanins, etc. (P. Ribéreau-Gayon, Plant Phenolics, Ed. Oliver & Boyd, Edinburgh, 1972, pp.169–198). These substances can be conjugated with simple phenols like e.g. gallic acids. These polyphenolic substances occur in tea stains, wine stains, banana stains, peach stains, etc. and are notoriously difficult to remove.

3. Carotenoids.

(G. E. Bartley et al., The Plant Cell (1995), Vol 7, 1027–1038). Carotenoids are the coloured substances which occur in tomato (lycopene, red), mango (β-carotene, orange-yellow). They occur in food stains (tomato) which are also notoriously difficult to remove, especially on coloured fabrics, when the use of chemical bleaching agents is not advised.

4. Anthocyanins.

(P. Ribéreau-Gayon, Plant Phenolics, Ed. Oliver & Boyd, Edinburgh, 1972, 135–169). These substance are the highly coloured molecules which occur in many fruits and flowers. Typical examples, relevant for stains, are berries, but also wine. Anthocyanins have a high diversity in glycosidation patterns.

5. Maillard Reaction Products

Upon heating of mixtures of carbohydrate molecules in the presence of protein/peptide structures, a typical yellow/brown coloured substance arises. These substances occur for example in cooking oil and are difficult to remove from fabrics.

6. Dyes in Solution.

For the prevention of dye transfer from a coloured piece of fabric to other garments during the wash, it valuable to specifically bleach the dye molecules in the wash solution. Several types of fabric dyes are used, and can therefore be envisaged to be a target for the oxidation process: e.g. sulphur dyes, vat dyes, direct dye, reactive dyes and azoic dyes.

The antibody of the invention granule contains an alkali metal salt, preferably a sodium salt. The preferred salt is sodium sulphate. The granules are manufactured using standard granulation technology, e.g. by mixing the ingredients in a mixing apparatus, preferably in the presence of a binder.

(a) The Enzyme

The antibody granules according to the invention may be used in a bleaching detergent composition. Such enzymatic detergent compositions comprise an oxidising or bleaching enzyme. The enzyme may either be an enzyme exhibiting peroxidase activity (which is then used together with a source of hydrogen peroxyde), or an enzyme exhibiting oxidase activity on phenolic compounds, such as a phenol oxidase or a laccase. Suitable enzymes are disclosed in EP-495 835 (Novo Nordisk). For instance, suitable peroxidases may be isolated from and are producible by plants or micro-organisms such as bacteria or fungi. Preferred fungi are strains belonging to the class of the *Basidiomycetes*, in particular *Coprinus*, or to the class of *Hyphomycetes*, in particular *Arthromyces*, especially *Arthromyces ramosus*. Other preferred sources are *Hormographiella* sp., *Myxococcus* sp., *Corallococcus* sp. (WO-A-95/11964), or Soybean peroxidase. Examples of suitable enzymes exhibiting oxidase activity on phenolic compounds are catechol oxidase and laccase and bilirubin oxidase. The laccase can be derived from fungi such as *Trametes* sp., *Collybio* sp., *Fomes* sp., *Lentinus* sp., *Pleurotus* sp., *Rhizoctonia* sp., *Aspergillus* sp., *Neurospora* sp., *Podospora* sp., *Phlebia* sp., *Coriolus* sp., *Myceliophthora* sp., *Coprinus* sp., *Panaeolus* sp., *Psathyrella* sp. (WO-A-96/06930). Bilirubin oxidase can be obtained from *Myrothecium* sp. or *Stachibotrys* sp.

The enzymatic oxidation compositions of the invention comprise about 0.001 to milligrams of active enzyme per litre. A detergent composition will comprise about 0.001% to 1% of active enzyme (w/w). The enzyme activity can be expressed as ABTS (2,2'-azino-bis(3-ethylbenzothiazoline-6-sulphonic acid) units. One ABTS unit represents the amount of enzyme which oxidizes ABTS, resulting in an increase of 1 optical density at 418 nm in one minute. Conditions for the activity assay are 2 mM ABTS, 1 mM $H_2O_2$, 20 mM Tris, pH 9. The enzyme activity which is added to the enzymatic oxidation composition will be about to $10^6$ ABTS units per litre, preferably $10^3$ to $10^5$ ABTS units per litre.

The oxidising enzymes can usefully be added to the detergent composition in any suitable form, i.e. the form of a granular composition, a liquid or a slurry of the enzyme, or with carrier material (e.g. as in EP-A-258 068 and the Savinase (TM) and Lipolase (TM) products of Novozymes). A good way of adding the enzyme to a liquid detergent product is in the form of a slurry containing 0.5 to 50% by weight of the enzyme in a ethoxylated alcohol nonionic surfactant, such as described in EP-A-450 702 (Unilever).

(b) The Source of Hydrogen Peroxide

If they contain a peroxidase, the enzymatic bleach or anti dye-transfer compositions according to the invention will also contain a source of hydrogen peroxide. This may be hydrogen peroxide itself, but more stabilized forms of hydrogen peroxide such as perborate or percarbonate are preferred. Especially preferred is sodium percarbonate.

Alternatively, one may employ an enzymatic hydrogen peroxide-generating system. The enzymatic hydrogen peroxide-generating system may in principle be chosen from the various enzymatic hydrogen peroxide-generating systems which have been disclosed in the art. For example, one may use an amine oxidase and an amine, an amino acid oxidase and an amino acid, cholesterol oxidase and cholesterol, uric acid oxidase and uric acid or a xanthine oxidase with xanthine. Preferably, however, the combination of a $C_1$–$C_4$ alkanol oxidase and a $C_1$–$C_4$ alkanol is used, and especially preferred is the combination of methanol oxidase and ethanol. The methanol oxidase is preferably isolated from a catalase-negative Hansenula polymorpha strain. (see for example EP-A-244 920 (Unilever)).

A third aspect of the invention is a process for preparing the antibody granules of the invention, in which an antibody is granulated with an alkali metal salt, preferably a potassium salt. It is preferred that the pH is kept at a value from 6.0 to 10.0, more preferably from 7 to 9. The process is preferably carried out at a temperature of 30° C. or higher, more preferably from 30° C. to 80° C., even more preferably from 30° C. to 65° C.

The invention will now be further illustrated in the following, non-limiting Examples.

EXAMPLE 1

A bi-head antibody (1249) was constructed (anti Glucose Oxidase—anti polyphenols/Red wine (Côtes du Rhone wine (Co-op, U.K.)) according to the method described in WO-A-99/23221 (Unilever). Granules were prepared with the lyophilized antibody 1249 to investigate the storage properties conferred by using different materials. The bi-head (containing Bicine and NaCl from ion exchange purification process) was combined with $Na_2SO_4$. The mixture was then thoroughly mixed and lightly ground in a pestle and mortar. 2.23 g of a 40% by weight solution of CP5 acrylate-maleate copolymer (ex BASF) was then added drop-wise to the solid mixture with frequent mixing. The 2.23 g was enough to cause the solids to "granulate" on mixing. The resultant granules were then transferred to a flat tray and left to dry in flowing air at room temperature. The granules lost 4.5% by weight on drying. The dry granules were then milled to less than 1000 micron.

Granule Composition:

| Material | wt % | % by weight |
|---|---|---|
| bi-head | 0.4 | 1.9 |
| NaCl/bicene | 1.227 | 5.9 |
| $Na_2SO_4$ | 18.453 | 88.0 |
| CP5 copolymer dry basis) | 0.892 | 4.3 |

Granules were also made with glucose instead of $Na_2SO_4$ or where 50% of the $Na_2SO_4$ was replaced with glucose.

Storage Trial

This was set up in fully formulated OMO MA powder, which was dispensed in amounts of 1 g/glass vial. Granules were dosed in at 50 milligram per vial. This was calculated to give approximately 1 mg/ml of bi-head when the contents of a vial were dissolved in 500 ml water. Labelled vials were placed in humidity chambers, for samples stored at room temperature (20° C.±2) the chamber contained a saturated solution of Potassium carbonate to provide about 44% humidity. For the samples stored at 37° C.±1, a saturated solution of NaCl was used to give about 75% humidity. Samples were removed at regular intervals and assayed for bi-spectic activity.

Assay for Bi-specific Activity

Microtitre Nunc Maxisorb plates were sensitized over night at 37° C. with 200 μl/well of red wine (Co-op, Côtes du Rhône). Six vials were removed from each humidity chamber using 2 of each granule type and the contents of each vial ere added to 500 ml of de-mineralized water. For a control, fresh granules were weighed out and added to 1 g of OMO MA, each was added to separate flasks containing 500 ml of demineralized water. The contents of each flask were stirred for minutes before a 250 μl aliquot was removed from each and diluted in PBST pH 7.4 to give 250 ng/ml bi-head.

Figure 1:
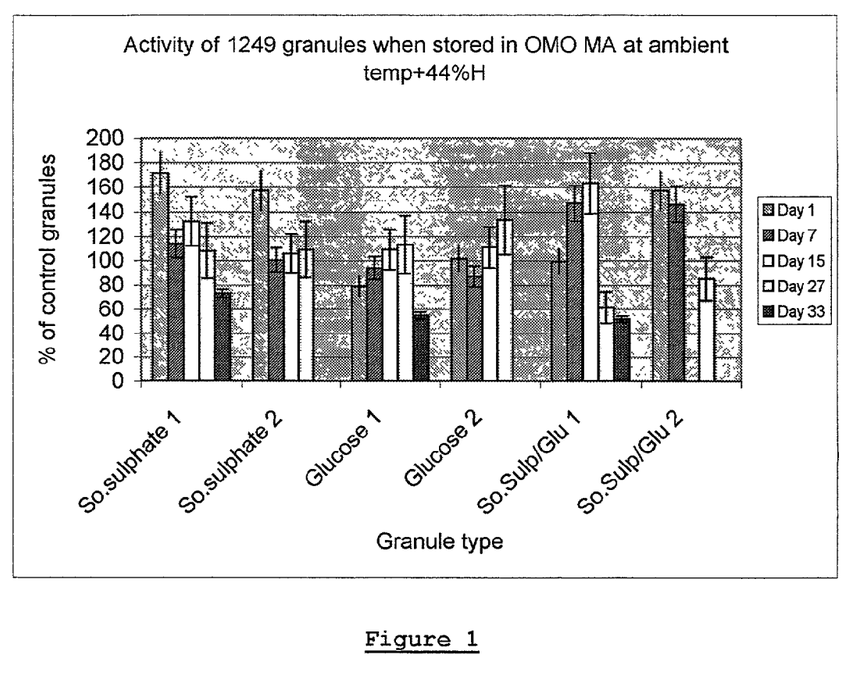
FIG. 1—Activity of various 1249 bihead granules after storage at room temperature.
Figure 2:
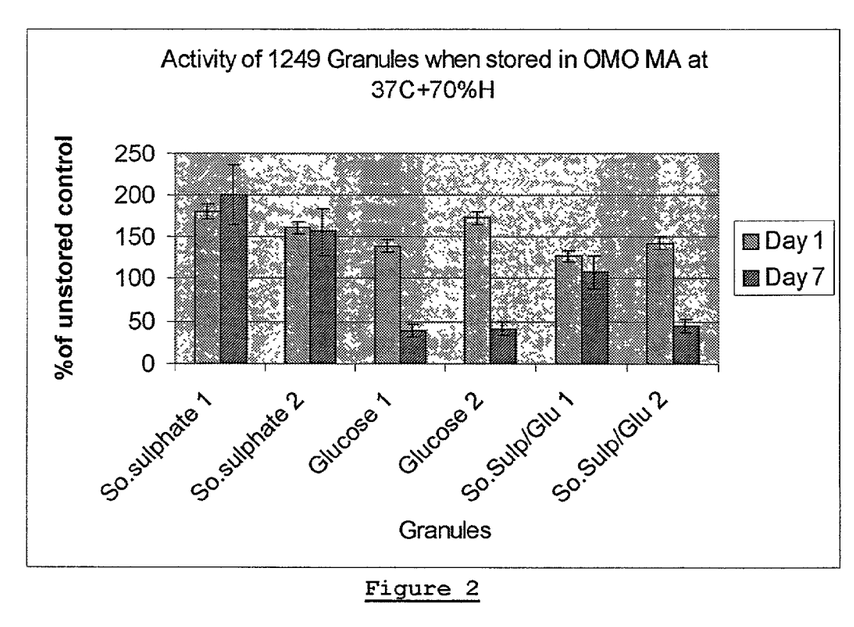
FIG. 2—Activity of the same granules after storage at 37° C./77%H.

Control and sample dilutions were dispensed at 200 μl per well in duplicate into the wells of washed red wine plates. After incubation of minutes at room temperature, the unbound samples were removed by three washes in PBST. Glucose oxidase (Gox) at 25 μg in PBST was dispensed to all wells containing sample and to additional wells that had previously been incubated only with PBST; this was to check for non-specific binding of the enzyme to the sensitized plate. Incubation was carried out for 1 hour and unbound Gox was removed by washing with PBST. Substrate containing TMB, 10 mM glucose and 2 μg/ml HRP was dispensed to each well and allowed to develop for minutes before the reaction was stopped by the addition of 10 μl/well of 1M HCl. Plates were read using a Dynatech plate reader at 450 nm. Duplicate readings from each dilution were averaged and plotted as a percentage of the appropriate control. The results are shown in FIGS. 1 and 2. They can be summarized as follows:

Granules stored at room temperature and containing sodium sulfate showed between 100 and 170% activity of that seen in the control samples. The glucose granules showed variability with one sample having 100% activity and other 80% activity. In subsequent assays a higher level of activity than the control sample was seen up until day 33. All granules tested showed a fall in activity to between 50 and 80% of the control.

All samples stored at 37° C. showed over 100% activity of the control samples. By day 7, the bihead granulated with sodium sulfate still showed binding levels above the control granules. The remaining samples showed a significant decrease in the bi-specific activity when compared to the appropriate controls. At assay on day 15, no activity was detected in any of the stored samples.

The storage conditions chosen were very different and the results obtained reflect this; at room temperature activity levels are still above 55% after 33 days. At 37° C. there is a dramatic drop off in activity between days 7 and 15. The effect of the ingredients following storage are variable, at 37° C./77% H, whereby the presence of glucose had a significant adverse affect on antibody activity (these granules showed a reduction in activity of up to 60%). The granules containing both sodium sulfate and glucose showed a similar trend. However, good activity was still detected on day 7 in the sodium sulfate granules and the same granules stored at room temperature/40% H had high antibody activity.

It was concluded that he granulation process with a simple salt did not detrimentally affect the activity of the bi-head. Also, storage of antibodies in a granulated form have a superior antibody activity as compared to conventional protein storage methods.

EXAMPLE 2

In this example, Bihead 1249 activity was investigated after granulation at different pH's. Bi-head 1249 granules were prepared as in Example 1. The bi-head activity of the granules was assessed with EIA. A Nunc maxisorb microtitre plate was sensitized overnight with Red wine by dispensing 200 μl of wine to each of the 96 wells and incubating at 37° C. Granules tested incorporated Bihead 1249 and one of the following salts:
sodium carbonate pH 10.4,
sodium bicarbonate pH 8.9,
sodium sulfate 7.2,
potassium sulfate pH 6,
potassium phosphate pH 5.8.

The granules samples were diluted to give a dilution curve with the following range, 50, 25, 12.5, 6.25, 3.125, 1.57, 0.785, 0.39, 0.196, 0.098 μg/ml in PBST. Each dilution was dispensed in duplicate into washed and sensitized wells and incubated for 30 minutes at room temperature before unbound sample was washed away.

Figure 3:
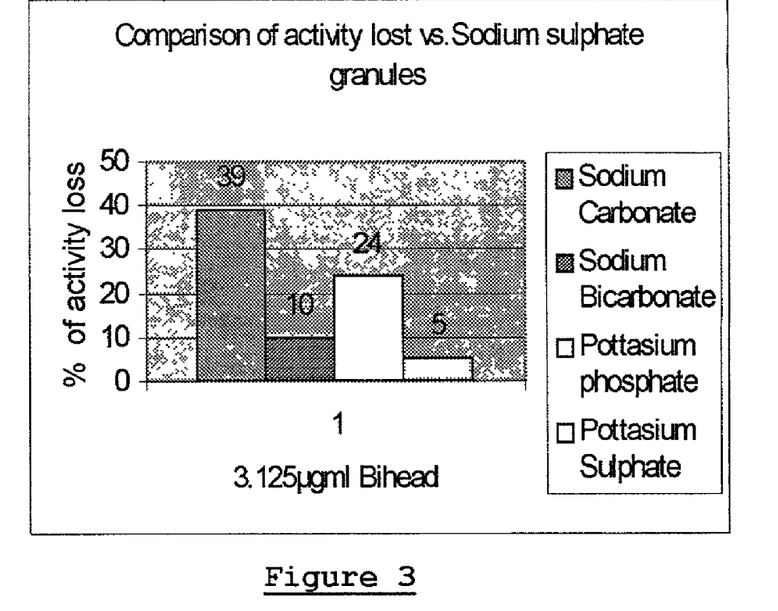
FIG. 3—Activity of various other granules 1249 after storage at room temperature.
Figure 4:
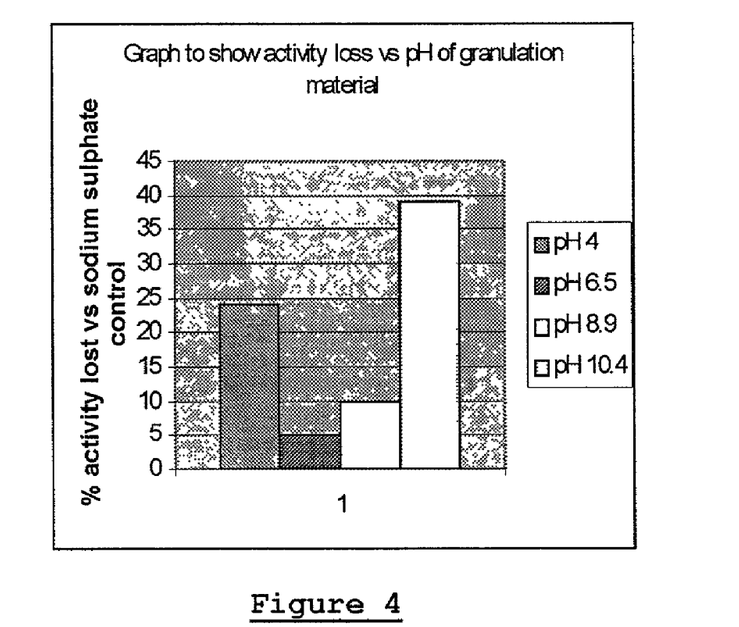
FIG. 4—Activity of 1249 granules as at various pH's.

Glucose oxidase at 25 μg/ml in PBST was dispensed into the wells and incubation was carried out for a further minutes. The plate was again washed with three changes of PBST before substrate buffer was added which comprised 10 mM Glucose, TMB and 2 µg/ml HRP was added. The reaction was stopped after minutes by the addition of 100 µl/well of 1M HCl. The plate was read at 450 nm. The results are shown in FIGS. 3 and 4. FIG. 3 shows the activity loss as a % relative to the sodium sulfate granules and FIG. 4 shows the activity loss at various pH values.

The largest loss is attributed to the granules with the highest and lowest pH's, although the remaining activity is still very good in these circumstances. At pH 6.5 there is very little difference compared to the control, this is the expected result since the pH of the granules is very similar. At pH 8.9 surprisingly little activity was lost.

EXAMPLE 3

The storage behaviour of Granulated Bihead at different pH's was investigated. $Na_2SO_4$ containing Bi-heads 1249 were prepared as in Example 1. Bihead concentration in dry granule was 1.94%. Using the same procedure the following variants were prepared:

(1) Sodium Bicarbonate

| Component | wt (g) |
| --- | --- |
| Bihead | 0.105 |
| Na Bicarbonate | 4.0 |
| CP5 | 0.302 |
| Salts etc | 0.395 |
| Bihead concentration in dry granule = 2.19% | |

(2) Potassium DiHydrogen Phosphate (pH=4)

| Component | wt (g) |
| --- | --- |
| Bihead | 0.07 |
| $KH_2PO_4$ | 2.8 |
| CP5 | 0.14 |
| Salts etc | 0.277 |
| Bihead concentration in dry granule = 2.13% | |

(3) Potassium Sulfate (use of the acidic builder CP45)

| Component | % |
| --- | --- |
| $KH_2PO_4$ | 82.5 |
| CP45 | 4.1 |
| Salts | 11.16 |
| Bi-Head | 2.22 |

Storage Trial

This was set up in OMO base powder, which was dispensed in amounts of 0.25 g/glass vial. Granules were dosed in at 50 mg per vial. This was calculated to give ~4 mg of bi-head when the contents of a vial were dissolved in 125 ml of water. Labeled vials were placed in humidity chambers, for samples stored at room temperature (20° C.±2) the chamber contained a saturated solution of Potassium carbonate to provide ~44% humidity. Temperature and humidity readings monitored with hygrometers. For the samples stored at 37° C.±1, a saturated solution of NaCl was used to give ~75% humidity. Samples were removed at regular intervals and assayed for bispecfic activity.

Assay Procedure

Microtitre Nunc Maxisorb plates were sensitized over night at 37° C. with 200 µl/well of red wine (Co-op, Côtes du Rhône). Ten vials were removed from each humidity chamber using 2 of each granule type. As control, fresh Omo base was weighed out and added to 125 ml of demineralised water, to this 4 mg of Bihead stock that had not been freeze dried was added. The contents of the stored vials were each added to 125 ml of demineralised water in 250 ml conical flasks. The solutions were stirred for minutes before a 250 µl aliquot was removed from each and diluted in PBST pH 7.4 to give 1 mg/ml bi-head. Control and sample dilutions were dispensed at 200 µl per well in duplicate into the wells of washed red wine plates and incubated for minutes at room temperature before the unbound protein was removed by three washes in PBST. Glucose oxidase (Gox) at 25 µg ml in PBST was dispensed to all wells containing sample and to additional wells that had previously been incubated only with PBST; this was to check for non-specific binding of the enzyme to the sensitized plate. Incubation was carried out for 1 hour; unbound Gox was removed by washing with PBST. Substrate containing TMB, 10 mM glucose and 2 µg/ml HRP was dispensed to each well and allowed to develop for 20 minute before the reaction was stopped by the addition of 10 µl/well of 1M HCl. Plates were read at 450 nm using a Dynatech plate reader. The samples were assayed at different intervals over a period of 60 days.

Figure 5:
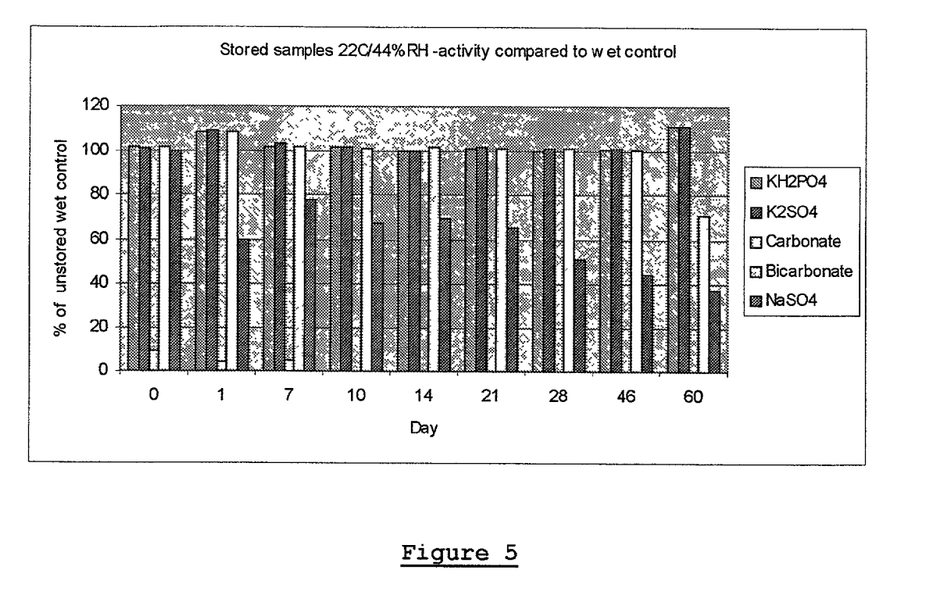
FIG. 5—Activity of 1249 granules after storage at room temperature.
Figure 6:
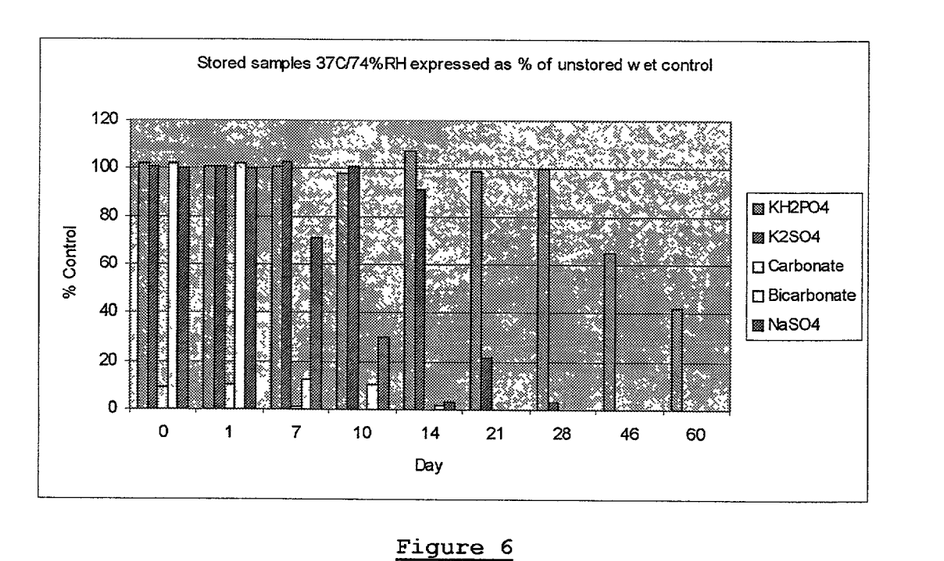
FIG. 6—Activity of 1249 granules after storage at 37° C./77%H.

For each sample the duplicate points were averaged and the standard deviation determined. To compare the activity of the different types of granule the readings from duplicate samples were averaged and compared to the wet control for activity. FIGS. 5 and 6 show % activity over 60 days for samples stored at 22° C. and 37° C.

Activity of the bihead was sustained over the storage period when potassium salts were included in the granulation process. There are some incidences of activity greater than 100% of the control but these are not significant. Bihead activity was also maintained to a high level when bicarbonate salts were incorporated into the granule. In the sample assayed at day 60 we detect a 30% decrease in the Bihead activity of the bicarbonate granules. The maintenance of bihead activity in the presence of Carbonate is very different by comparison. The activity in these granules was measured on day 0, to be 9.1% of the control. This low level of activity is probably due to the very basic environment of the granule causing conformational changes in the first instance and protein breakdown in the longer term.

Figure 7:
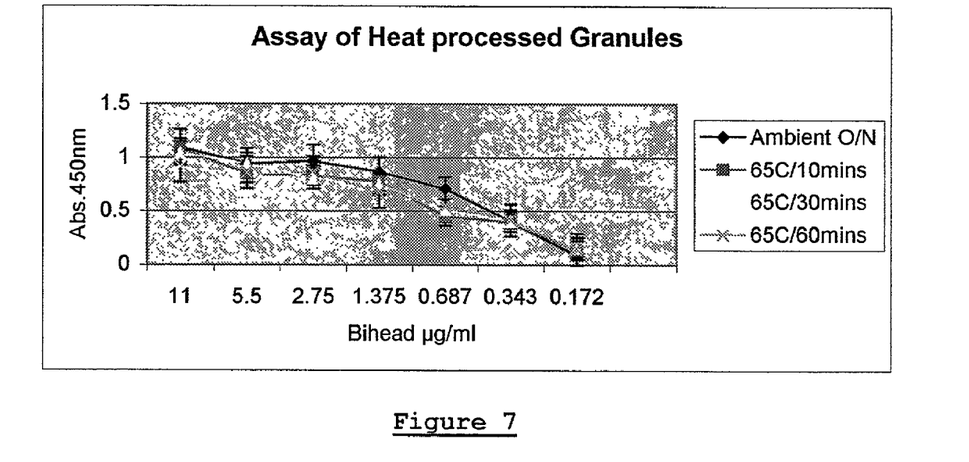
FIG. 7—Assay of heat-processed 1249 granules.

The effect of sodium sulfate in bihead granules was also studied in example 1, wherein lower concentrations of bihead were measured over a storage period of 33 days. This trial yielded similar results, the bihead activity was between 60–80% from days 1–28 but started falling below 50% by day 46. In these conditions the favoured components would be either of the potassium salts or bicarbonate. The results of storage at 37° C. vary greatly and are summarized in FIG. 7. From this data it is evident that the carbonate granules are very low in activity at day 0 and therefore were not tested after day 1. The potassium variants again show outstanding Bihead activity, with these conditions we are able to determine that the potassium sulfate granules show a reduction in Bihead activity by day 14 and by day 21 there is a significant decrease (~90%) in the activity detected, by day 28 less than 10% of the control activity was measured. By contrast the potassium phosphate granules maintain Bihead activity at 100% of the control until day 46, when there is a decrease of ~40%. The last measurement on day 60 still detected 40% of bihead activity in these granules. The use of the acidic builder CP45 may be contributory in the lack of stability here. The bihead showed less stability in the bicarbonate granules in these conditions, with very little activity remaining on day 14. With sodium sulfate the activity loss was also complete by day 14 but the loss was more gradual than with the severe drop seen with bicarbonate. In these conditions, potassium phosphate maintains bihead activity longer than any of the other components tested.

At 37° C. the potassium phosphate granules absorbed moisture from the storage environment. However, this did not appear to affect the activity of the bihead. The high pH of the carbonate granule inactivated the Bihead during normal storage at low humidity and is, therefore, totally unsuitable for use during the granulation of Bihead.

EXAMPLE 4

Comparison of granules processed at different temperatures. Bihead 1249 granules were prepared with the aim of looking at the effect of various processing procedures and to see if drying time can be kept to a minimum by the use of increased temperatures. This would be advantageous since the use of heat with enzyme preparation is normally detrimental to enzyme activity. The following 1249 bihead granules were

| prepared: | |
|---|---|
| Bihead 1249 | 0.21 |
| Na$_2$SO$_4$ | 8.0 |
| CP5 | 0.37 |
| 20 Salts etc | 0.872 |

Bihead concentration in the dry granule was 2.22%. The sulfate granules were split into 4 separate fractions, each of which was dried under different conditions. These were:

a) Over night at room temp in flowing air
b) min at 65° C. in an oven
c) min at 65° C. in an oven
d) 60 min at 65° C. in an oven The activity was measured using the same method as given in Example 2. The samples were diluted to give 11 µgml in PBST, this was then double diluted to give a range for assay. The results are given in FIG. 7. It was found that the temperature used for drying has not significantly affected the activity of the bihead. Samples dried for minutes give the same assay result as those dried for an hour. The sample dried overnight at ambient temperature gives a slightly higher reading, but this is statistically not significant.

The invention claimed is:

1. A process for preparing an antibody granule consisting essentially of granulating one or more antibodies, or fragments derived thereof, with a solid alkali metal salt, and an acrylate/maleate copolymer binder, wherein the antibody granule contains more than 80 wt. % alkali metal salt.

2. The process according to claim 1, wherein the alkali metal is sodium or potassium.

3. The process according to claim 1, wherein the antibody has a chemical equilibrium constant $K_d$ for its antigen of less than $1*10^{-4}$.

4. The process according to claim 1, wherein the antibody has a chemical equilibrium constant $K_d$ for its antigen of less than $1*10^{-7}$.

5. The process according to claim 1, where in the granulating temperature is 30° C. or higher.

6. The process according to claim 1, wherein the granulating pH is kept at a value from 6.0 to 10.0.

7. The process according to claim 1, wherein the antibody granule contains more than 90 wt. % alkali metal salt.

8. The process according to claim 1, wherein the antibody has a chemical equilibrium constant $K_d$ for its antigen of less than $1*10^{-6}$.

9. Process according to claim 1, wherein the granulating temperature is from 30° C. to 80° C.

10. Process according to claim 1, wherein the granulating pH is kept at a value from 7.0 to 9.0.

* * * * *